United States Patent [19]
Estay

[11] Patent Number: 5,492,220
[45] Date of Patent: Feb. 20, 1996

[54] APPARATUS FOR SUPPORTING A CUP WHEN TAKING URINE SAMPLES

[76] Inventor: Debbie L. Estay, 3482 W. Moark, Springfield, Mo. 65810

[21] Appl. No.: 315,221

[22] Filed: Sep. 29, 1994

[51] Int. Cl.⁶ .................................................... A45F 5/00
[52] U.S. Cl. ........................................ 206/363; 294/137
[58] Field of Search ................................... 206/363, 438; 220/737, 738; 294/137, 165, 166, 167

[56] References Cited

U.S. PATENT DOCUMENTS

| | | | |
|---|---|---|---|
| 2,654,628 | 10/1953 | Klante | 294/137 |
| 3,986,648 | 10/1976 | Antonini et al. | 206/363 X |
| 4,331,357 | 5/1982 | Contreras | 294/166 X |

Primary Examiner—Jacob K. Ackun, Jr.

[57] ABSTRACT

An apparatus for supporting a cup when taking urine samples comprising an elongated cylindrical central component having a distal end and a proximal end; a support ring in a generally circular configuration with a circular cross section secured at one exterior peripheral extent at its proximal end to the distal end of the central component, the ring component having an opening extending therethrough at about ninety degrees from the point of contact between the central component and the ring component, the opening constituting about one and ten degrees of the ring; and a handle in a generally rectangular configuration having a proximal end and a distal end with the distal end being coupled with respect to the proximal end of the central component.

5 Claims, 4 Drawing Sheets

FIG. 5
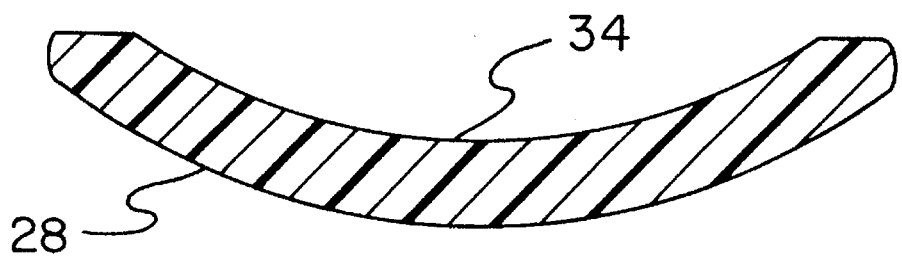
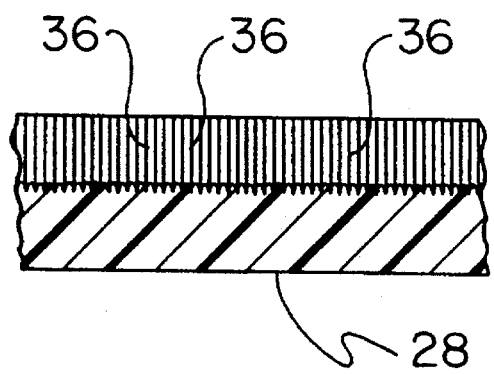
FIG. 6

5,492,220

APPARATUS FOR SUPPORTING A CUP WHEN TAKING URINE SAMPLES

BACKGROUND OF THE INVENTION

1. Field of the Invention

The present invention relates to an apparatus for supporting a cup when taking urine samples and more particularly pertains to supporting a urine sample cup in a proper orientation in a sanitary, reliable, and convenient manner.

2. Description of the Prior Art

The use of devices for supporting and holding objects of a wide variety of designs and configurations is known in the prior art. More specifically, devices for supporting and holding objects of a wide variety of designs and configurations heretofore devised and utilized for the purpose of supporting objects in a desired orientation through a holding device through a wide variety of methods and apparatuses are known to consist basically of familiar, expected, and obvious structural configurations, notwithstanding the myriad of designs encompassed by the crowded prior art which has been developed for the fulfillment of countless objectives and requirements.

U.S. Pat. No. 4,033,489 discloses a disposable cup holder.

U.S. Pat. No. 5,029,720 discloses a combined cup and holder.

U.S. Pat. No. Des. 271,073 discloses the design of a cup holder.

In this respect, the apparatus for supporting a cup when taking urine samples according to the present invention substantially departs from the conventional concepts and designs of the prior art, and in doing so provides an apparatus primarily developed for the purpose of supporting a urine sample cup in a proper orientation in a sanitary, reliable, and convenient manner.

Therefore, it can be appreciated that there exists a continuing need for a new and improved apparatus for supporting a cup when taking urine samples which can be used for supporting a urine sample cup in a proper orientation in a sanitary reliable convenient manner. In this regard, the present invention substantially fulfills this need.

SUMMARY OF THE INVENTION

In view of the foregoing disadvantages inherent in the known types of devices for supporting and holding objects of a wide variety of designs and configurations now present in the prior art, the present invention provides an improved apparatus for supporting a cup when taking urine samples. As such, the general purpose of the present invention, which will be described subsequently in greater detail, is to provide a new and improved apparatus for supporting a cup when taking urine samples and method which has all the advantages of the prior art and none of the disadvantages.

To attain this, the present invention essentially comprises a new and improved apparatus for supporting a cup when taking urine samples comprising, in combination, an elongated cylindrical central component having a distal end and a proximal end; a support ring in a generally circular configuration with a circular cross section secured at one exterior peripheral extent at its proximal end to the distal end of the central component, the ring component having an opening extending therethrough at about ninety degrees from the point of contact between the central component and the ring component, the opening constituting about one and ten degrees of the ring; a handle in a generally rectangular configuration having a proximal end and a distal end with the distal end being coupled with respect to the proximal end of the central component, the handle having a dished curvature along its length with the center of curvature being located above the handle a distance substantially equal to the length of the central component, the handle being formed with transverse ridges along the length thereof and an unridged periphery thereabout, the central section being about 125 and 175 percent of the length of the handle; circumferential ribs formed in the ring at its interior extent to facilitate the grasping of a cup thereby; and a transparent package receiving and supporting one of the holders in a sealed, sanitary manner with sealed ends to ensure the retention of the sanitary condition of the holder therein.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved apparatus for supporting a cup when taking urine samples which has all the advantages of the prior art devices for supporting and holding objects of a wide variety of designs and configurations and none of the disadvantages.

It is another object of the present invention to provide a new and improved apparatus for supporting a cup when taking urine samples which may be easily and efficiently manufactured and marketed.

It is further object of the present invention to provide a new and improved apparatus for supporting a cup when taking urine samples which is of durable and reliable construction.

An even further object of the present invention is to provide a new and improved apparatus for supporting a cup when taking urine samples which is susceptible of a low cost of manufacture with regard to both materials and labor, and which accordingly is then susceptible of low prices of sale to the consuming public, thereby making such apparatus for supporting a cup when taking urine samples economically available to the buying public.

Still yet another object of the present invention is to provide a new and improved apparatus for supporting a cup when taking urine samples which provides in the apparatuses and methods of the prior art some of the advantages thereof, while simultaneously overcoming some of the disadvantages normally associated therewith.

Still another object of the present invention is to support a urine sample cup in a proper orientation in a sanitary reliable convenient manner.

Lastly, it is an object of the present invention to provide a new and improved apparatus for supporting a cup when taking urine samples comprising an elongated cylindrical central component having a distal end and a proximal end; a support ring in a generally circular configuration with a circular cross section secured at one exterior peripheral extent at its proximal end to the distal end of the central component, the ring component having an opening extending therethrough at about ninety degrees from the point of contact between the central component and the ring component, the opening constituting about one and ten degrees of the ring; and a handle in a generally rectangular configuration having a proximal end and a distal end with the distal end being coupled with respect to the proximal end of the central component.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a cross-sectional view taken along line 5—5 of FIG. 3.

FIG. 6 is a cross-sectional view taken along line 6—6 of FIG. 2.

The same reference numerals refer to the same parts through the various Figures.

DESCRIPTION OF THE PREFERRED EMBODIMENT

Figure 1:
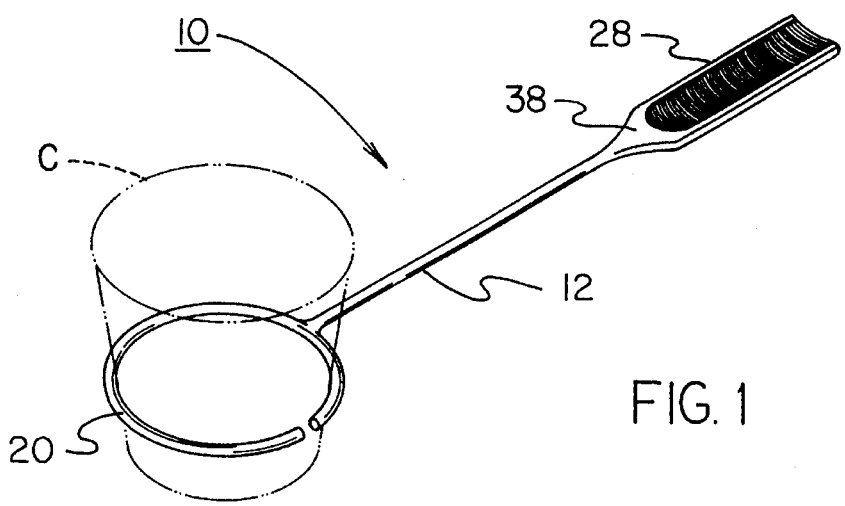
FIG. 1 is a perspective view of the preferred embodiment of the new and improved apparatus for supporting a cup when taking urine samples constructed in accordance with the principles of the present invention.
Figure 2:
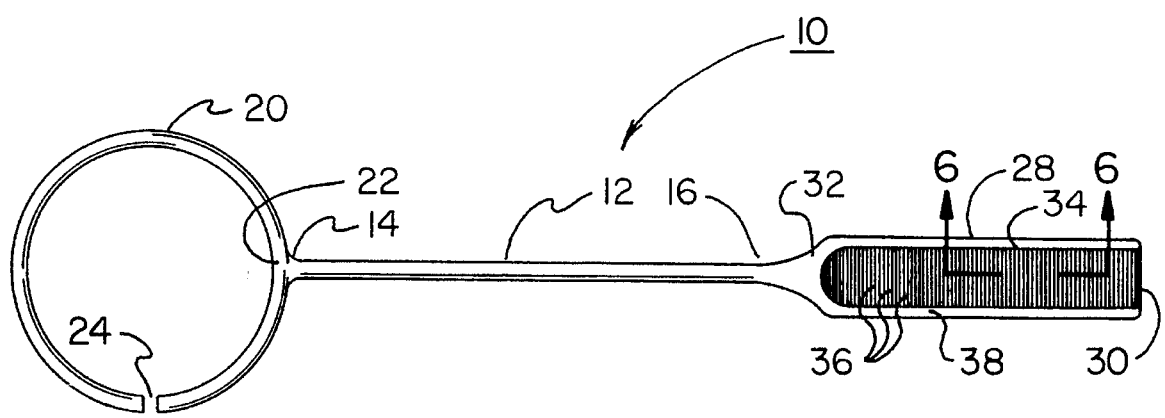
FIG. 2 is a top elevational view of the device shown in FIG. 1.
Figure 3:
FIG. 3 is a side elevational of the device shown in FIGS. 1 and 2.
Figure 4:
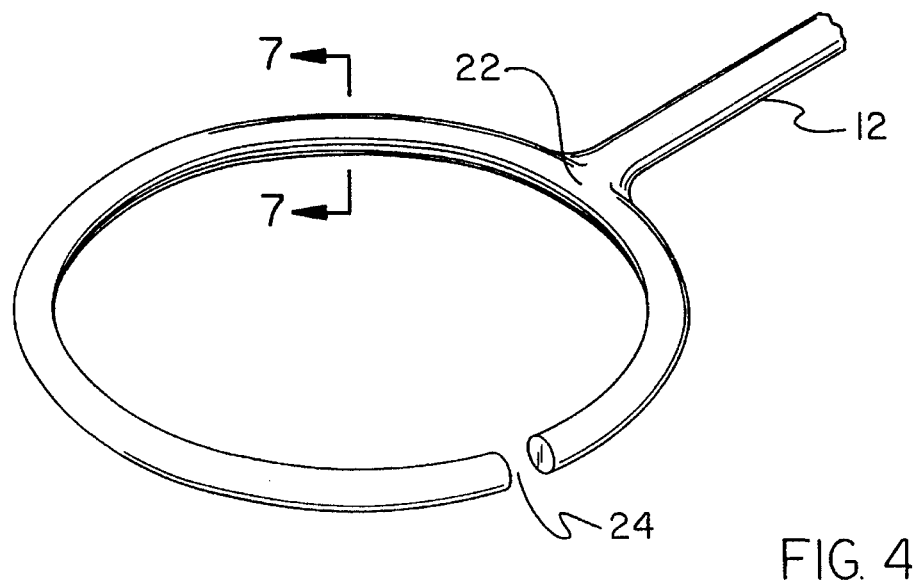
FIG. 4 is an enlarged perspective of the head portion of the device of the prior Figures.

With reference now to the drawings, and in particular to FIG. 1 thereof, the preferred embodiment of the new and improved apparatus for supporting a cup when taking urine samples embodying the principles and concepts of the present invention and generally designated by the reference numeral 10 will be described.

The present invention, the new and improved apparatus for supporting a cup when taking urine samples, is a system 10 comprised of a plurality of components. Such components, in their broadest context, include a cylindrical central component, support ring, handle, ribs and package. Such components are individually configured and correlated with respect to each other so as to attain the desired objective.

The central component of the system 10 is an elongated cylindrical central component 12. Such component has a distal end 14 and a proximal end 16. Associated with the central component is a support ring 20. The support ring 20 is in a generally circular configuration with a circular cross-section. The support ring is secured at one exterior peripheral extent at its proximal end 22 to the distal end 14 of the central component 12. The ring component has an opening 24 extending therethrough. Such opening is located at about ninety degrees from the point of contact between the central component and the ring component. The opening constitutes between about one and ten degrees of the ring. This opening allows a slight flexing of the ring to accommodate the support of cutting of various sizes.

Next provided in association with the central component 12 is a handle 28. The handle is in a generally rectangular configuration. It has a proximal end 30 and a distal end 32. The distal end is coupled with respect to the proximal end of the central component 12.

The handle has a dished curvature 34 along its length with the center of the curvature being located above the handle at a distance substantially equal to the length of the central component. The handle is formed with transverse ridges 36 along the length thereof. This facilitates the handling thereof by a user. The handle also has an unridged periphery 38 around the ridged portion. The central section is about 125 and 175 percent of the length of the handle.

Figure 7:
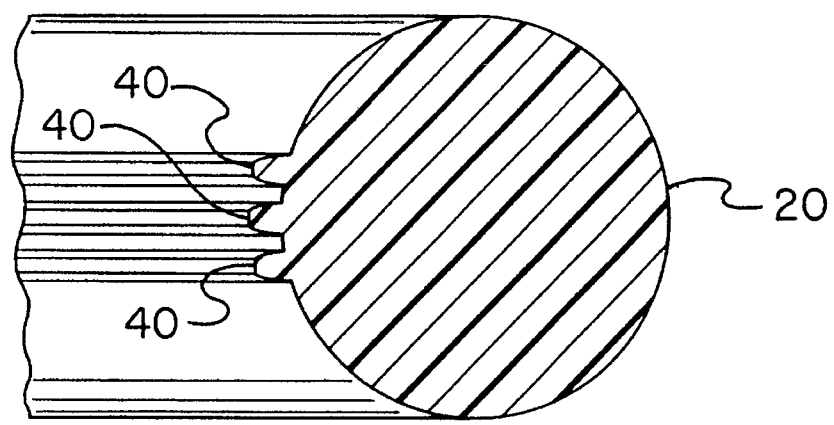
FIG. 7 is a cross-sectional view taken through the ring of the prior Figures but illustrating an alternate embodiment of the invention.
Figure 8:
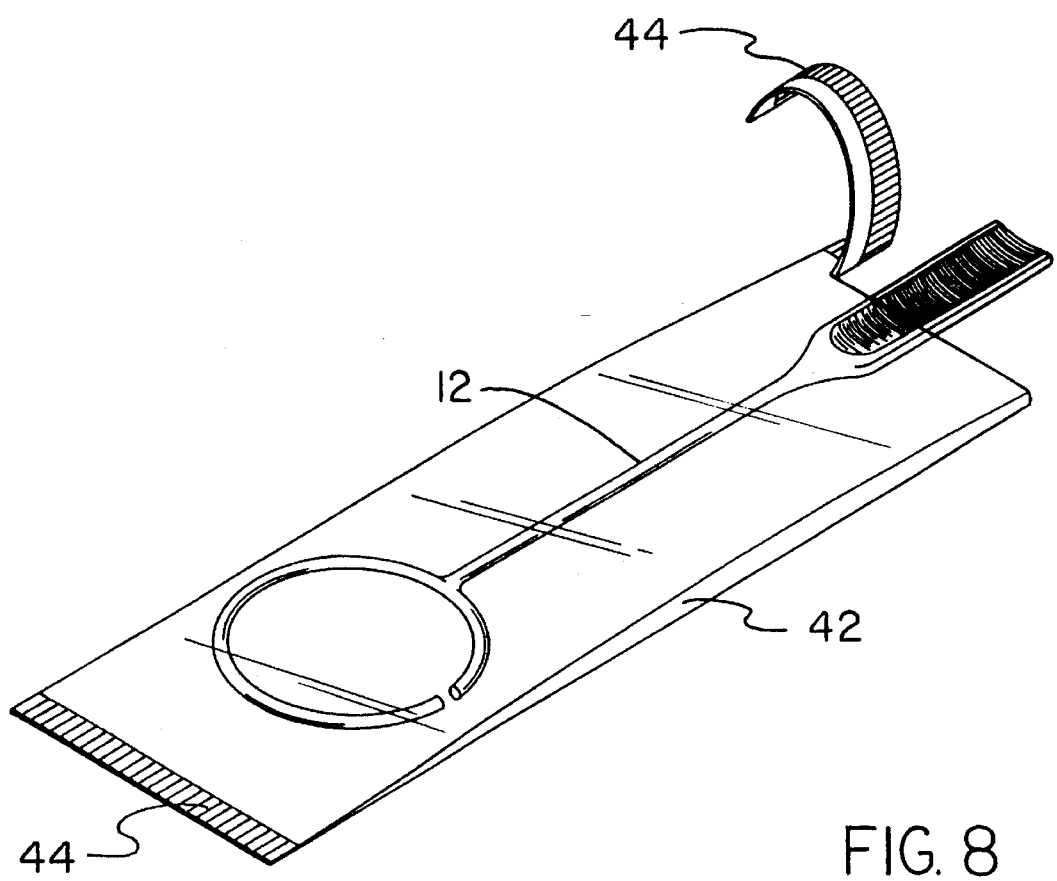
FIG. 8 is a perspective illustration of the device of the prior Figures but located in a sanitary package for retention and dispensing.

Greater facility is provided to the device 10 of the present invention by the inclusion of circumferential ribs 40. Such ribs can be seen in FIG. 7. Such ribs are formed in the ring at its interior extent. Such ribs facilitate the secure grasping of the cup by the ring. Lastly, a transparent package 42 is preferably provided. Such package is fabricated of a flexible transparent material for receiving and supporting one of the holders in a sealed, sanitary manner. The ends 44 of the package are sealed to ensure the retention of the sanitary condition of the holder therein.

The present invention comprises a cup holder which enables women to give urine samples in a more sanitary and convenient way. The present invention can measure up to 6 inches to 12 inches in length. It can be made of many materials including plastic, wood, cardboard, metal, glass or fiberglass, or vinyl. The handled end of the cup holder can be flat and wide, round and larger than neck, round and flat, square and flat, rectangular and flat, small flat loop, etc.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved apparatus for supporting a cup when taking urine samples comprising, in combination:

an elongated cylindrical central component having a distal end and a proximal end;

a support ring in a generally circular configuration with a circular cross section secured at one exterior peripheral extent at its proximal end to the distal end of the central component, the ring component having an opening extending therethrough at about ninety degrees from the point of contact between the central component and the ring component, the opening constituting about one and ten degrees of the ring;

a handle in a generally rectangular configuration having a proximal end and a distal end with the distal end being coupled with respect to the proximal end of the central component, the handle having a dished curvature along its length with the center of curvature being located above the handle a distance substantially equal to the length of the central component, the handle being formed with transverse ridges along the length thereof and an unridged periphery thereabout, the central section being about 125 and 175 percent of the length of the handle;

circumferential ribs formed in the ring at its interior extent to facilitate the grasping of a cup thereby; and a transparent package receiving and supporting one of the holders in a sealed, sanitary manner with sealed ends to ensure the retention of the sanitary condition of the holder therein.

2. An apparatus for supporting a cup when taking urine samples comprising:

an elongated cylindrical central component having a distal end and a proximal end;

a support ring in a generally circular configuration with a circular cross section secured at one exterior peripheral extent at its proximal end to the distal end of the central component, the ring component having an opening extending therethrough at about ninety degrees from the point of contact between the central component and the ring component, the opening constituting about one and ten degrees of the ring; and a handle in a generally rectangular configuration having a proximal end and a distal end with the distal end being coupled with respect to the proximal end of the central component.

3. The device as set forth in claim 2 wherein the handle has a curvature along its length with the center of curvature being located above the device a distance substantially equal to the length of the central section, the handle being formed with transverse ridges along the length thereof and an unridged periphery thereabout.

4. The device as set forth in claim 2 and further including:

circumferential ribs formed in the ring at its interior extent to facilitate the grasping of a cup thereby.

5. The device as set forth in claim 2 and further including:

a transparent package receiving and supporting one of the holders in a sealed, sanitary manner with clipped ends to ensure the retention of the sanitary condition of the holder therein.

* * * * *